US010080612B2

(12) United States Patent
Kappel et al.

(10) Patent No.: US 10,080,612 B2
(45) Date of Patent: Sep. 25, 2018

(54) INSTRUMENT HOLDER

(71) Applicant: Boston Scientific Scimed, Inc., Maple Grove, MN (US)

(72) Inventors: Gary Kappel, Acton, MA (US); Barry Weitzner, Acton, MA (US); Paul Smith, Smithfield, RI (US); Erin Daly, Nashua, NH (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 453 days.

(21) Appl. No.: 14/615,568

(22) Filed: Feb. 6, 2015

(65) Prior Publication Data

US 2015/0150632 A1 Jun. 4, 2015

Related U.S. Application Data

(63) Continuation of application No. 13/326,585, filed on Dec. 15, 2011, now Pat. No. 8,979,826.

(Continued)

(51) Int. Cl.
*A61B 17/00* (2006.01)
*A61B 19/00* (2006.01)
(Continued)

(52) U.S. Cl.
CPC ........ *A61B 19/201* (2013.01); *A61B 1/00149* (2013.01); *A61B 17/00234* (2013.01);
(Continued)

(58) Field of Classification Search
CPC ......... A61B 50/20; A61B 50/22; A61B 50/24; A61B 5050/21; A61B 90/50; A61B 90/57;
(Continued)

(56) References Cited

U.S. PATENT DOCUMENTS 2,437,916 A 3/1948 Greenwald
3,299,883 A 1/1967 Rubens
(Continued)

FOREIGN PATENT DOCUMENTS

AU 2007-234512 A1 12/2007
DE 10307054 A1 9/2004

OTHER PUBLICATIONS

PCT International Search Report and PCT Written Opinion of the International Searching Authority for corresponding PCT application PCT/US2011/067507, dated Apr. 10, 2012, 12 pages.

(Continued)

*Primary Examiner* — Ahmed Farah
(74) *Attorney, Agent, or Firm* — Bookoff McAndrews, PLLC

(57) ABSTRACT

A support mechanism for a medical device may include an adjustable support that includes a plurality of elongate members movable relative to one another. The support mechanism may also include a bracket coupled to the adjustable support. The bracket may be adapted to be coupled to a first medical device that extends along a longitudinal axis. The support mechanism may also include an instrument holder that extends along a central axis. The instrument holder may be movably coupled to the bracket and adapted to be coupled to a second medical device. The bracket and the instrument holder may be oriented such that central axis of the instrument holder intersects the longitudinal axis at an angle.

17 Claims, 8 Drawing Sheets

Related U.S. Application Data

(60) Provisional application No. 61/427,946, filed on Dec. 29, 2010.

(51) Int. Cl.
*A61B 90/50* (2016.01)
*A61B 90/11* (2016.01)
*A61B 50/20* (2016.01)
*A61B 1/00* (2006.01)

(52) U.S. Cl.
CPC .............. *A61B 50/20* (2016.02); *A61B 90/11* (2016.02); *A61B 90/50* (2016.02); *A61B 1/0014* (2013.01)

(58) Field of Classification Search
CPC .......... A61B 2090/571; A61B 1/00131; A61B 1/0014; A61B 1/00147; A61B 1/00149; A61B 1/00154; A61B 1/001
USPC ............... 606/1; 600/101, 102, 104, 114
See application file for complete search history.

(56) References Cited

U.S. PATENT DOCUMENTS

| | | | |
|---|---|---|---|
| 4,813,401 A | 3/1989 | Grieshaber | |
| 4,867,404 A | 9/1989 | Harrington et al. | |
| 5,100,387 A | 3/1992 | Ng | |
| 5,224,680 A | 7/1993 | Greenstein et al. | |
| 5,269,305 A | 12/1993 | Corol | |
| 5,337,731 A | 8/1994 | Takahashi et al. | |
| 5,441,042 A * | 8/1995 | Putman ............... | B25J 9/042 600/102 |
| 5,571,072 A | 11/1996 | Kronner | |
| 5,758,650 A | 6/1998 | Miller et al. | |
| 5,779,623 A | 7/1998 | Bonnell | |
| 5,797,835 A * | 8/1998 | Green ............... | A61B 17/3401 600/106 |
| 5,820,623 A * | 10/1998 | Ng ................ | A61B 34/70 606/1 |
| 5,957,423 A | 9/1999 | Kronner | |
| 6,149,583 A | 11/2000 | Vierra et al. | |
| 6,223,100 B1 * | 4/2001 | Green ................ | B25J 3/04 348/E13.014 |
| 6,916,000 B2 | 7/2005 | Weiss | |
| 6,957,423 B1 | 10/2005 | Ma | |
| 6,969,392 B2 | 11/2005 | Gitis et al. | |
| 6,994,703 B2 | 2/2006 | Wang et al. | |
| 7,022,082 B2 | 4/2006 | Sonek | |
| 7,137,949 B2 | 11/2006 | Scirica et al. | |
| 7,670,281 B2 | 3/2010 | Kronner | |
| 8,979,826 B2 * | 3/2015 | Kappel .............. | A61B 1/00149 600/102 |
| 2002/0007188 A1 | 1/2002 | Arambula et al. | |
| 2004/0220588 A1 * | 11/2004 | Kermode .......... | A61B 10/0041 606/129 |
| 2005/0267373 A1 | 12/2005 | Lee | |
| 2006/0253109 A1 | 11/2006 | Chu | |
| 2007/0293734 A1 * | 12/2007 | Coste-Maniere ...... | B25J 9/1671 600/300 |
| 2008/0086150 A1 * | 4/2008 | Mathis .................. | A61B 90/57 606/130 |
| 2008/0183034 A1 | 7/2008 | Henkin et al. | |
| 2008/0188868 A1 | 8/2008 | Weitzner et al. | |
| 2009/0023985 A1 | 1/2009 | Ewers | |
| 2009/0163766 A1 | 6/2009 | Torrie et al. | |
| 2009/0312775 A1 * | 12/2009 | Gilkey .................. | A61B 1/018 606/147 |
| 2009/0326555 A1 | 12/2009 | Vohra et al. | |
| 2010/0185212 A1 | 7/2010 | Sholev | |
| 2010/0286478 A1 | 11/2010 | Ewers et al. | |
| 2011/0282358 A1 | 11/2011 | Gomez et al. | |
| 2012/0118088 A1 * | 5/2012 | Smith ................ | A61B 1/00154 74/89.2 |

OTHER PUBLICATIONS

Kappel, G. and Stanton, L., Instrument Control Device, U.S. Appl. No. 13/297,675, filed Nov. 28, 2011, 35 pages.

Smith, P., Weitzner, B., Daly, E., Kappel, G. and Golden, J., Bearing Assembly for Instrument, U.S. Appl. No. 13/304,916, filed Nov. 16, 2011, 61 pages.

* cited by examiner

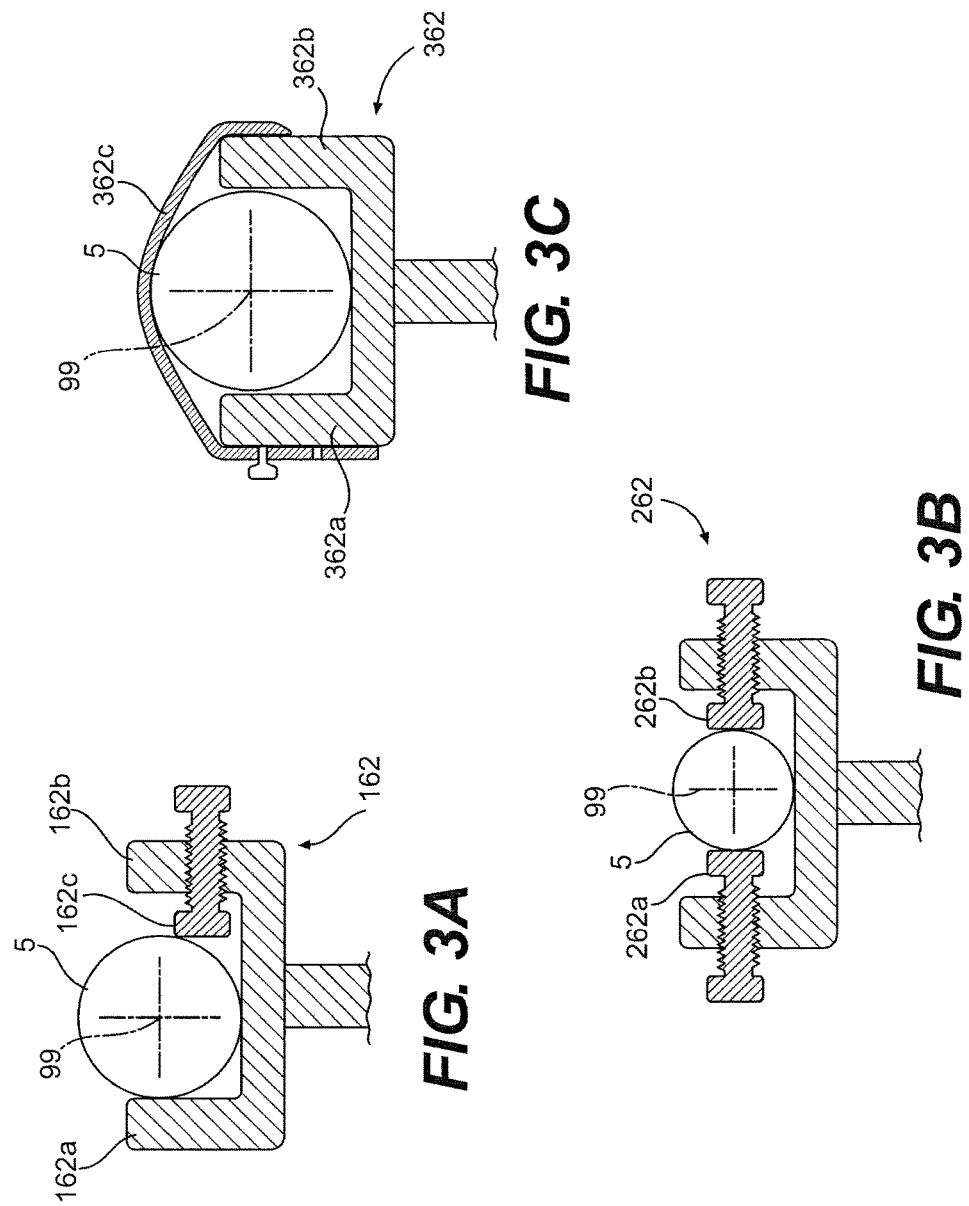

INSTRUMENT HOLDER

CROSS-REFERENCE TO RELATED APPLICATIONS

This application is a continuation of U.S. application Ser. No. 13/326,585, filed on Dec. 15, 2011, incorporated herein by reference in its entirety, which claims the benefit of priority under 35 U.S.C. § 119(e) of U.S. Provisional Application No. 61/427,946 to Kappel et al. filed on Dec. 29, 2010.

FIELD OF THE INVENTION

Embodiments of the invention include holding devices for medical instruments and more particularly holding devices that permit proximal divergence of medical instruments coupled thereto, and related methods of use.

BACKGROUND OF THE INVENTION

Minimally invasive surgical instruments, such as endoscopic and laparoscopic devices, can provide access to surgical sites while minimizing patient trauma. Although the growing capabilities of such therapeutic and diagnostic devices allow physicians to perform an increasing variety of surgeries through traditional minimally invasive routes, further refinements may increase the effectiveness of these surgeries by increasing their ease of use. Currently some robotic systems have been proposed to control such surgical instruments while performing surgery. Such systems, however, fail to provide the tactile feedback to the user and may only enable limited degrees of freedom for the instruments. Accordingly, there is room for further refinement to conventional minimally invasive surgical devices and a need to develop new surgical systems.

It is to be understood that both the foregoing general description and the following detailed description are exemplary and explanatory only and are not restrictive of the invention.

SUMMARY OF THE INVENTION

In one embodiment, a support mechanism for a medical device is disclosed. The support mechanism may include an adjustable support that includes a plurality of elongate members movable relative to one another. The support mechanism may also include a bracket coupled to the adjustable support. The bracket may be adapted to be coupled to a first medical device (such as a guide for receiving instruments) that extends along a longitudinal axis. The support mechanism may also include an instrument holder that extends along a central axis. The instrument holder may be movably coupled to the bracket and adapted to be coupled to a second medical device. The bracket and the instrument holder may be oriented such that central axis of the instrument holder intersects the longitudinal axis at an angle.

Various embodiments of the invention may also include an arm that slidably couples the instrument holder to the bracket, wherein sliding one of the instrument holder and the bracket on the arm changes a spacing between the instrument holder and the bracket and the angle; the bracket may include a mechanism that is adapted to latch to the first medical instrument; the bracket may include a substantially U-shaped cross-sectional shape along a plane transverse to the longitudinal axis; the instrument holder may include a substantially tubular component that extends along the central axis; a cross-sectional shape of the instrument holder along a plane transverse to the central axis may be substantially C-shaped; increasing a spacing between the bracket and the instrument holder may increases the angle; the arm may include a plurality of features that are configured to mate with a mating feature on at least one of the instrument holder and the bracket to lock the at least one of the instrument holder and the bracket at a fixed location on the arm; and an angular orientation of the longitudinal axis and the central axis with respect to a horizontal plane may be adjustable.

According to another embodiment, a method of using a medical device on a patient is disclosed. The method may include inserting a distal end of a first instrument into the patient. The first instrument may extend along a longitudinal axis. The method may also include inserting a distal end of a second instrument that extends along a central axis into a port of the first medical instrument. The port may extend at an angle from a side of the first instrument. The method may also include positioning the first instrument and the second instrument such that distal portions of the first instrument and the second instrument extend into the patient along the longitudinal axis and a proximal portion of the second instrument makes an angle with the longitudinal axis. The method may further include supporting a proximal end of the first instrument on a bracket of a support mechanism, and supporting a proximal end of the second instrument on an instrument holder of the support mechanism. The instrument holder may be movably coupled to the bracket.

Various embodiments of the invention may also include inserting a distal end of a third instrument into a second port of the first instrument, wherein the second port extends at a second angle from the longitudinal axis, and supporting a proximal end of the third instrument on a second instrument holder of the support mechanism; supporting the first instrument may include supporting the first instrument on the bracket in a hands-free manner; and changing a spacing between the bracket and the instrument holder. In some embodiments, the method may further include translation of the second instrument relative to the instrument holder. The second instrument may be movably coupled to the instrument holder.

According to a further embodiment, a support mechanism for a medical device is disclosed. The support mechanism may include a first instrument holder having a first central axis configured to support a first instrument that extends along the first central axis in a hands-free manner. The support mechanism may also include a second instrument holder having a second central axis that intersects the first central axis. The second instrument holder may be configured to support a second instrument that extends along the second central axis in a hands free manner. The support mechanism may also include an arm that movably couples the first instrument holder to the second instrument holder.

Various embodiments of the invention may include: a third instrument holder movably coupled to the first instrument holder and having a third central axis that intersects with the first central axis; the first central axis, the second central axis, and the third central axis may intersect at substantially the same location; the arm may movably couple both the second instrument holder and the third instrument holder to the first instrument holder; the second instrument holder may be configured to slidably couple to the second instrument; the support mechanism may further include an adjustable support that includes a plurality of elongate members movable relative to one another and rotatably coupled to the first instrument holder, wherein rotating the first instrument holder on the plurality of elongate members changes an angular orientation of the first central axis with respect to a horizontal plane; at least one of the first instrument holder and the second instrument holder may include a substantially U-shaped cross-sectional shape along a transverse plane; the support mechanism may further include the first instrument coupled to the first instrument holder and the second instrument slidably coupled to the second instrument holder, wherein the first instrument may include a first cavity that extends along the first central axis and a first port that extends at a first angle from a side of the first instrument, and wherein a distal portion of the second instrument may extend along the first central axis within the first cavity and a proximal portion of the second instrument may exit the first cavity through the first port and extends along the second central axis.

Additional objects and advantages of the invention will be set forth in part in the description which follows, and in part will be obvious from the description, or may be learned by practice of the invention. The objects and advantages of the invention will be realized and attained by means of the elements and combinations particularly pointed out below.

It is to be understood that both the foregoing general description and the following detailed description are exemplary and explanatory only and are not restrictive of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

FIGS. 3A-3C are cross-sectional illustrations of exemplary brackets that may be used in the holding device of FIG. 2;

DESCRIPTION OF THE EMBODIMENTS

Reference will now be made in detail to exemplary embodiments of the invention, examples of which are illustrated in the accompanying drawings. Wherever possible, the same reference numbers will be used throughout the drawings to refer to the same or like parts.

The terms "proximal" and "distal" are used to refer to the relative positions of the components of the exemplary endoscopy system 10 discussed herein. When used herein, "proximal" refers to a position relatively closer to the exterior of the body or closer to the surgeon using the endoscopy system 10. In contrast, "distal" refers to a position relatively further away from the surgeon using the endoscopy system 10 or closer to the interior of the body. In addition, while the discussion of systems and methods below may generally refer to "surgical instruments," "surgery," or a "surgical site" for convenience, the described systems and their methods of use are not limited to surgical operations. The described systems and methods may also be used for diagnostic or other purposes in addition to, or as an alternative to, surgical purposes. Although various exemplary treatment devices and methods are discussed or referred to herein, their application is not limited to any particular treatment. Additionally, although the disclosed devices and methods are discussed in a medical context, it is also contemplated that some embodiments of the devices may perform non-medical operations.

Figure 1A:
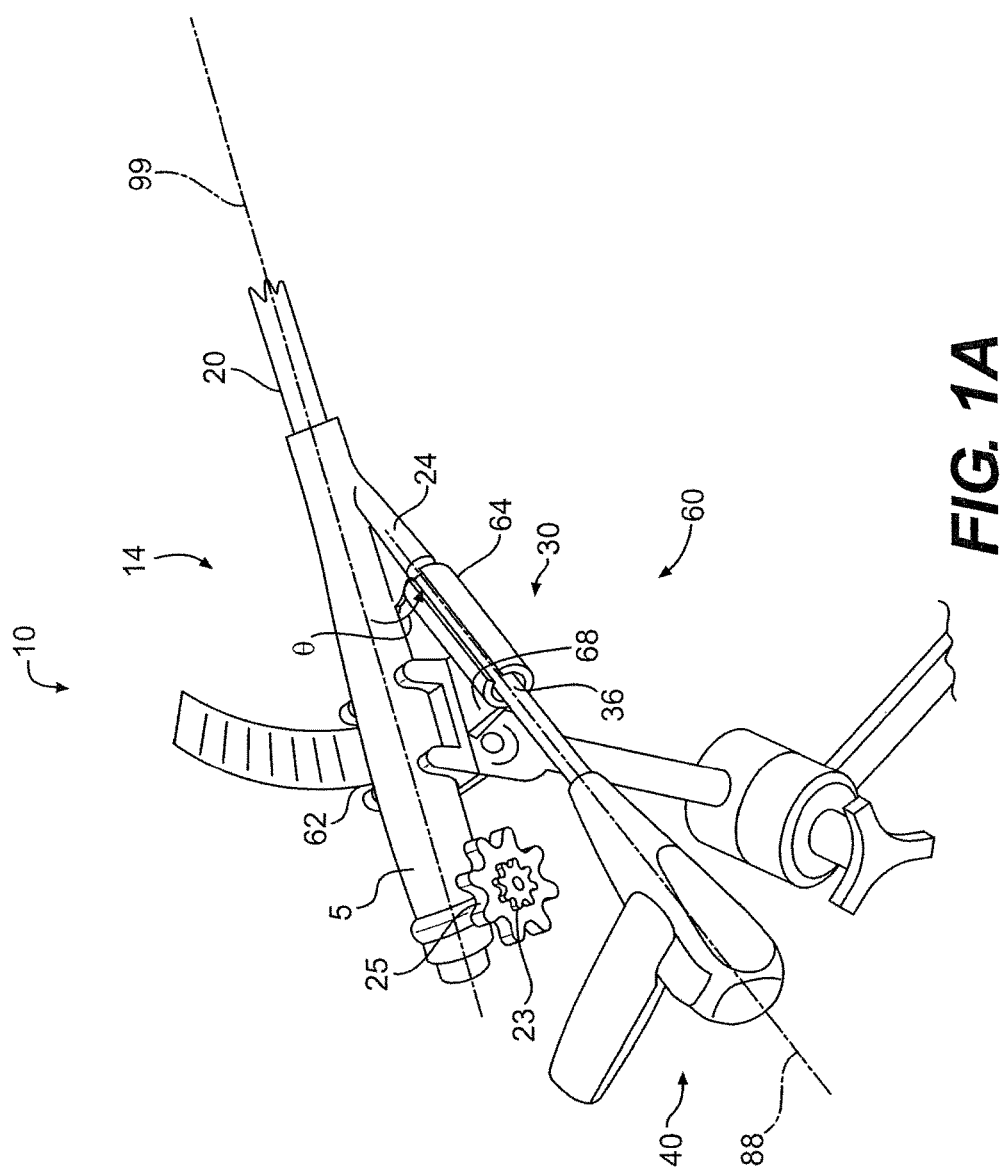
FIG. 1A is a perspective view of a proximal end of an endoscopy system including an exemplary instrument holder.
Figure 1B:
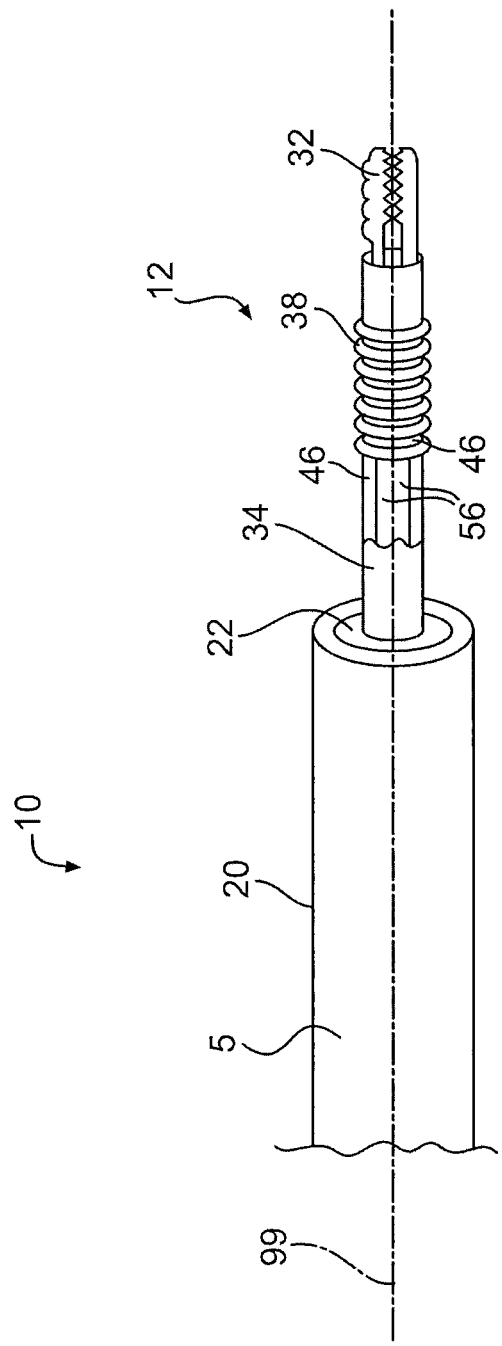
FIG. 1B is a perspective view of a distal end of the endoscopy system of FIG. 1A.

FIGS. 1A and 1B depict an exemplary endoscopy system 10 and related components that may be used for therapeutic and/or diagnostic endoscopic procedures. The phrase "endoscopic procedure" is broadly used to indicate any medical procedure that may be performed by inserting an endoscope, guide tube, catheter, or any such medical device into the body through any natural, surgical, percutaneous, or any other opening in the body. The term "endoscopic system" is also used broadly to include all components and systems that may be used for the endoscopic procedure. The endoscopy system 10 may be used for performing a diagnostic or therapeutic operation within the body by a surgeon (or another operator) controlling the endoscopy system 10 from outside the body. The endoscopy system 10 may be applicable to any endoscopic application known in the art. Non limiting examples of such endoscopic applications may include trans-oral, trans-anal, trans-vaginal, trans-urethral, trans-nasal, transluminal, laparoscopic, thorascopic, orthopedic, aural, percutaneous, or other applications. The components of the endoscopy system 10 described below may be made of any suitable material capable of being inserted into the body, e.g., a suitable biocompatible material.

As shown in FIGS. 1A and 1B, the endoscopy system 10 may include an endoscope 5 (laparoscope, catheter, guide tube, etc.) having an elongate member 20 having one or more channels 22 that extend therethrough (FIG. 1B). Although only one channel 22 is illustrated in the elongate member 20 of FIG. 1B, other embodiments of endoscopes may include a plurality of channels. The channel 22 may extend substantially longitudinally (axially) within the elongate member 20 between a distal end 12 and a proximal end 14. The elongate member 20 may be configured to be advanced through any body cavity or body lumen of a patient. The elongate member 20 may be flexible, for example, to be able to traverse the tortuous anatomy of a body cavity.

FIG. 1A illustrates the proximal end 14 of endoscopy system 10 positioned external to the body. FIG. 1B illustrates the opposite distal end 12 of the endoscopy system 10 positioned internal to the body. In the discussion below, reference will be made to both FIGS. 1A and 1B. The surgeon may control the operation of the distal end 12 by activating controls or devices at the proximal end 14. Although not illustrated in the embodiment of FIG. 1B, endoscope 5 may include imaging, illumination, and other capabilities (such as, for example, suction, irrigation, etc.). The imaging capability may include a camera or another imaging device (CMOS, CCD, optical fiber, etc.) positioned at distal end 12. The imaging device may be configured to acquire an image of the body proximate the distal end 12 and transmit the image to an imaging device positioned at the proximal end 14. The illumination systems may also include light sources (LED, LCD, etc.) that are configured to illuminate the body proximate the distal end 12 to aid the imaging device. Elongate member 20 may include cables or wires that electrically couple these imaging and illumination devices to supporting systems (power supplies, display devices, etc.) positioned at proximal end 14. It is also contemplated that, in some embodiment, the images may be send remotely. Suction and irrigation capabilities may include systems that provide vacuum and fluid to the distal end 12 to aid in an application of endoscope 5. Since these and other capabilities of endoscopes are well known in the art, for the sake of brevity, they are not further discussed herein.

Endoscope 5 may also include structure for steering the elongate member 20 through a body cavity. This structure may include rotatable control knobs 23, 25 positioned at the proximal end 14 of the endoscope 5. These knobs 23, 25 may connect control wires or cables (not shown) that extend through the elongate member 20 to provide steering of the distal end 12 of the elongate member 20. The knobs 23, 25 may be manipulated by a surgeon to bend and flex the distal end 12 of the endoscope 5 as it navigates through a body cavity.

One or more instruments 30 may be inserted through the channel 22 in the elongate member 20 at proximal end 14. The proximal end 14 of endoscope 5 may include one or more ports 24 that open into channel 22. These one or more ports 24 may provide access to the channels 22 that extend longitudinally through elongate member 20. Although only one port 24 is illustrated in the embodiment of FIG. 1A, other embodiments may include multiple ports 24. In some embodiments, one or more of these ports may include fluid seals. An instrument 30 may be slidably inserted through port 24 to enter channel 22. As shown in FIG. 1A, in some embodiments, port 24 may be provided at an angle θ to the longitudinal axis 99 of elongate member 20. In some embodiments, as illustrated in FIG. 1A, a central axis 88 of port 24 may make a fixed angle θ with respect to the longitudinal axis 99, while in other embodiments, angle θ may be variable. To insert instrument 30 into channel 22, a distal end of the instrument 30 may be inserted into port 24, and the instrument 30 pushed in to slide the distal end of the instrument down channel 22.

To position the elongate member 20 and the instrument 30 at an internal site within the body of a patient, the distal end of the elongate member 20 may be first inserted into an opening in the patient and advanced into the patient (e.g., advanced into a body organ, through a body lumen, etc.) through a percutaneous port, to position the distal end 12 at the desired location inside the body. The instrument 30 may then be inserted into port 24 and advanced through channel 22 so that the distal end of the instrument 30 protrudes through channel 22 at the distal end 12. In some embodiments, the distal end of channel 22 may include a seal (not shown), and the distal end of the instrument 30 may extend out of channel 22 through the seal. Alternatively, the instrument 30 may be advanced through the elongate member 20 before the elongate member 20 is inserted into the opening in the patient.

As shown in FIG. 1B, the instrument 30 may include an end effector 32 attached to a distal end of an elongate member 34 that extends through channel 22. A portion of elongate member 34 is shown without its outer sheath to expose cables 46, 56 that extend therethrough. These cables 46, 56 may enable a surgeon to activate the end effector 32 using controls at the proximal end 14. The end effector 32 may include any device known in the art that is configured to assist in performing a desired endoscopic or surgical procedure. Non-limiting examples of such end effectors 32 may include scissors, forceps, needles, closure devices, sutures, retrieval devices, etc. The instrument 30 may include a proximal portion 36 and a distal portion 38. In some embodiments, the distal portion 38 may be relatively more flexible than the proximal portion 36. In embodiments where the central axis 88 of port 24 makes an angle θ with the longitudinal axis 99 of channel 22, the flexible distal portion 38 may enable instrument 30 to bend through angle θ and enter the channel 22 from port 24. The flexible distal portion 38 may also enable the instrument 30 to traverse through curved sections of channel 22 when the endoscope 5 is positioned in a curved body tract. The relatively more rigid proximal portion 36 may enable the proximal portion 36 to be coupled to an instrument holder 64 (FIG. 1A) at proximal end 14 without buckling. Coupling the proximal portion 36 of the instrument 30 in instrument holder 64 may permit hands-free operation of instrument 30. That is, this may allow the surgeon to leave the instrument 30 in place, while providing stabilization and control to the instrument, when the surgeon releases the instrument 30.

In some embodiments, the distal portion 38 and the proximal portion 36 include continuous lengths of the elongate member 34 at the distal end 12 and the proximal end 14 respectively. In other embodiments, the distal portion 38 and/or the proximal portion 36 may include discrete lengths of elongate member 34 that are separated by a stretch of elongate member 34 having a different rigidity. The distal portion 38 and the proximal portion 36 may be dimensioned to provide a stop that limits the longitudinal movement of instrument 30. For example, the diameters (and/or the cross-sectional shape) of the proximal portion 36 and the distal portion 38 may be such that the proximal portion 36 is prevented from entering port 24. In other embodiments, another mechanism, such as for example a protrusion in the proximal portion 36 may limit the longitudinal movement of instrument 30. The instrument 30 may also include an activation mechanism 40 (for example, a handle) at the proximal end 14. The activation mechanism 40 may be coupled to the end effector 32 using the cables 46, 56 that extend through elongate member 34. Activation mechanism 40 may include any type of control mechanism known in the art (such as, for example, scissors-type handle, thumb-ring and spool-type handle, etc.). Since such activation mechanisms are known in the art, they are not further discussed herein. By activating the activation mechanism 40, the surgeon may control the movement (translation and rotation) and/or the articulation (opening, closing, etc.) of the end effector 32.

The endoscopy system 10 may further include a holding device 60 (FIG. 1A) for supporting and positioning the endoscope 5 and the instrument 30. The holding device 60 may be configured to position the endoscope 5 and instrument 30 in a variety of configurations based on the preference of the surgeon. In some of these configurations, both the endoscope 5 and the instrument 30 may move together as one body, while in other configurations, the endoscope 5 may move with respect to the instrument 30 (or vice versa). The surgeon may choose a suitable configuration based on, among others, the patient location, the operation being performed, and ergonomic factors. As shown in FIG. 1A, the holding device 60 may include a bracket 62 and one or more instrument holders 64. Although only one bracket 62 and one instrument holder 64 is illustrated in the embodiment of holding device 60 illustrated in FIG. 1A, other embodiments may include a plurality of brackets and/or instrument holders spaced apart from each other.

Figure 2:
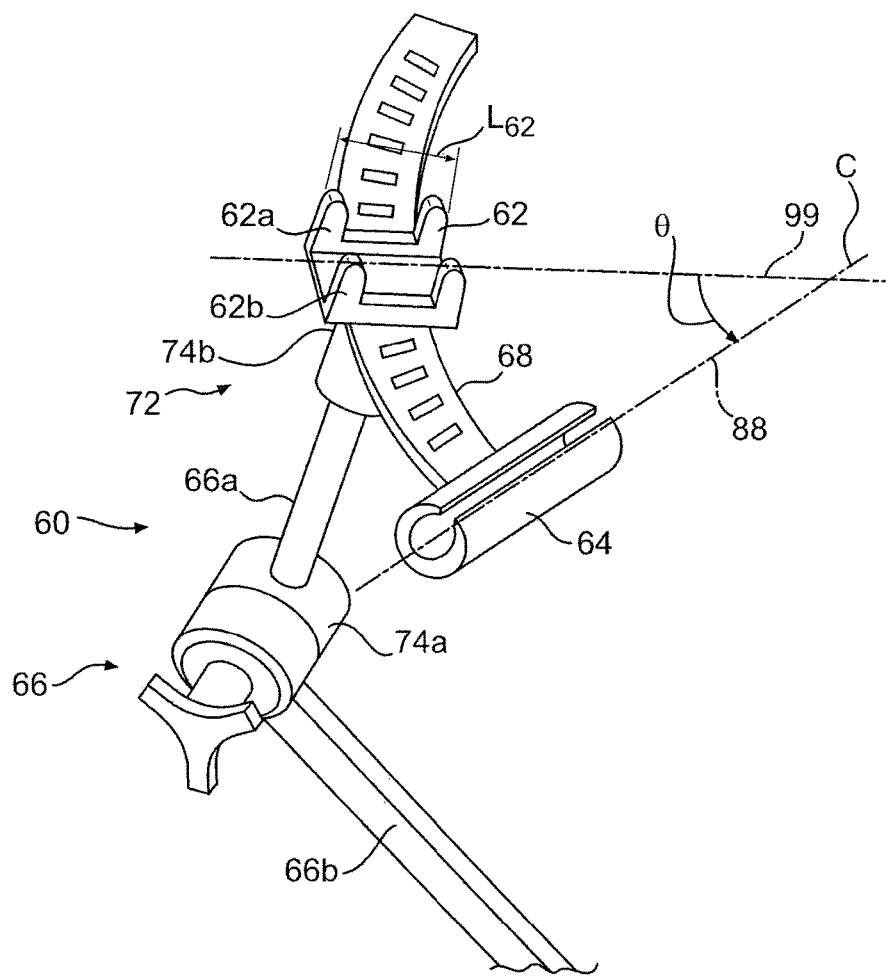
FIG. 2 is a perspective view of an exemplary holding device of the endoscopy system of FIG. 1A.

FIG. 2 is an illustration of an exemplary holding device 60 with the elongate member 20 and instrument 30 removed therefrom for clarity. Instrument holder 60 may include an adjustable support 66 that may be adapted to vary the orientation (such as, for example, height, rotation, etc.) of a top section 72 of the holding device 60. The adjustable support 66 may include members 66a, 66b that may be coupled together by one or more hinges, such as, for example, hinges 74a, 74b. Hinge 74a may be configured to adjust the orientation of member 66a with respect to member 66b, and hinge 74b may be configured to adjust the orientation of the top section 72 with respect to member 66a. Although two members 66a, 66b coupled together by a hinge 74a that is adapted to rotate the members in one plane is illustrated in FIG. 2, this is only exemplary. In general, holding device 60 may include any number of members coupled together by any number of hinges. These hinges may be adapted to rotate one or more of the members with respect to another in multiple planes. One or more of the members may also include a telescoping section adapted to change a length of the member. Together, these members and hinges may be configured to vary the height and the angular orientation of the top section 72 of holding device 60 with respect to a horizontal plane (such as, for example, the ground or another surface the instrument holder 60 is resting on). Adjustable support 66 may also include stops and/or locking mechanisms that are configured to limit (or lock) the motion of one or more members (or lock) of the adjustable support 66. For example, in the embodiment of FIG. 2, loosening a knob coupled to hinge 74a may allow member 66a to be rotated with respect to member 66b, and tightening the knob may lock and fix the orientation of member 66a with respect to member 66b. The bottom portion (not shown) of the adjustable support may include features that are adapted to attach to another structure, such as, for example, the operating table, the bed of a patient, etc. In some embodiments, the bottom portion of adjustable support 66 may include a stand or legs that are adapted to support the adjustable support 66 on a floor or another surface. It is also contemplated that, in some, embodiments, the bottom portion of adjustable support 66 may include straps or other features that are adapted to attach to the body of the patient or the surgeon treating the patient.

Top section 72 of the holding device 60 may include the bracket 62 that is configured to support the endoscope 5, and the instrument holder 64 that is configured to support the instrument 30. Bracket 62 may have any shape that is adapted to support endoscope 5. In some embodiments, bracket 62 may slidably support endoscope 5 and have a length $L_{62}$ that is sufficient to support endoscope 5 in a stable and hands-free manner. Bracket 62 may include extensions 62a and 62b that are adapted to securely hold the endoscope 5 therebetween. The bracket 62, along with extensions 62a and 62b, may include a generally c-shaped cross-sectional shape along a plane transverse to the longitudinal axis 99 of the elongate member 20. The extensions may be sized to snugly fit the endoscope 5 therebetween. In some embodiments, the endoscope 5 may snap in place between the extensions 62a and 62b, and the resilience of the extensions 62a, 62b may securely hold the endoscope 5 in place. In these embodiments, the resilience of the extensions 62a, 62b may provide the frictional force necessary to prevent the unrestrained sliding of the endoscope 5 in the bracket 62. Other embodiments of bracket 62 may include other mechanisms to support and stabilize the endoscope 5.

FIGS. 3A-3C show some other embodiments of brackets that may be used with a holding device 60 of the current disclosure. Bracket 162 of FIG. 3A may include a screw-like movable extension 162c that may be moved to enable endoscopes 5 (or elongate members 20) having different sizes to be securely supported. In some embodiments, as illustrated by bracket 262 of FIG. 3B, in place of moveable extension 162c, one or both of extensions 262a and 262b may be moveable to support an endoscope 5 therebetween. In some embodiments, as illustrated in FIG. 3C, a strap 362c may securely support endoscope 5 in bracket 362. The strap 362c may include slots or other features along its length that are configured to mate with a corresponding feature (such as, a protrusion as illustrated in FIG. 3c) on bracket 362 to enable different sized endoscopes to be coupled thereto. In these embodiments, the force exerted by the parts of the bracket (such as, for example, the extensions, straps, etc.) on the endoscope 5 may prevent the unrestrained sliding of the endoscope 5 in the bracket. It should be emphasized that the embodiments of brackets illustrated in FIGS. 3A-3C are only exemplary, and in general, any structure that may be used to support endoscope 5 in a stable manner may be used as bracket 62. For example, in some embodiments, instead of a strap, a cover may bear down on the endoscope to securely support the endoscope. Although in the discussion above, a retention force applied by bracket 62 on the endoscope 5 is described as preventing the unrestrained sliding of the endoscope 5 on the bracket 62, this is only exemplary. In some embodiments, a locking mechanism (such as, for example, a set-screw or a tab/groove on bracket 62 that mates with a corresponding groove/tab on the endoscope 5) may prevent the unrestrained sliding of the endoscope 5 on the bracket 62.

Figure 4A:
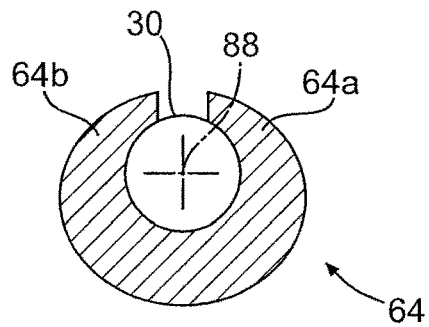
FIG. 4A-4C are cross-sectional illustrations of exemplary instrument holders that may be used in the holding device of FIG. 2.
Figure 4B:
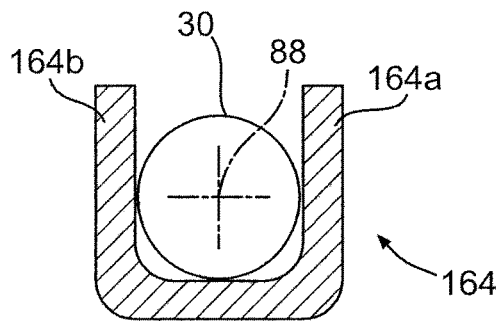
Figure 4C:
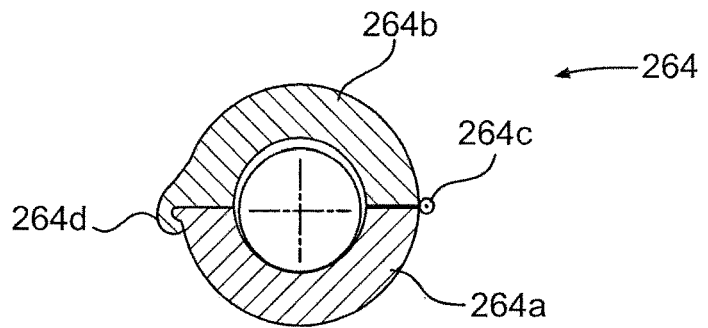

With reference to FIG. 2, instrument holder 64 may include any structure that is configured to securely hold the instrument 30 therein. In some embodiments, instrument 30 may be slidably coupled to instrument holder 64. FIGS. 4A-4C illustrate cross-sectional views of some exemplary embodiments of instrument holders that may be used with a holding device of the current disclosure. FIG. 4A shows an embodiment of instrument holder 64 that has a substantially C-shaped cross-sectional shape (along a plane transverse to the central axis 88 of instrument 30) having extensions 64a and 64b. These extensions 64a, 64b may have flexibility (by material choice, cross-sectional design, etc.) and may be spread apart to allow the instrument 30 to pass into the space therebetween. When instrument 30 is secured in the instrument holder 64, the extensions 64a and 64b may apply sufficient force on the instrument to prevent the unrestrained sliding of the instrument 30 on the instrument holder 64. FIG. 4B illustrates another exemplary embodiment of instrument holder 164 having a substantially U-shaped cross-sectional shape. As in the embodiment of FIG. 4A, the instrument 30 may be snugly held between the extensions 164a and 164b of instrument holder 164. FIG. 4C shows another embodiment of instrument holder 264 that uses a clamp 264b to securely hold the instrument 30 thereon. One end of clamp 264b may be pivoted on slide 264a at pivot 264c and an opposite end of clamp 264b may include a clasp 264d that engages with a corresponding feature on slide 264a. Together, clamp 264b and slide 264a may slidably secure an instrument therein. The embodiments of instrument holders illustrated in FIGS. 4A-4C are only exemplary, and in general, any structure (such as those illustrated in FIGS. 3A-3C) that can support instrument 30 in a stable and hands-free manner may be used as instrument holder 64. In some embodiments, the instrument holder 64 may also include a locking mechanism (such as, for example, a set-screw or tabs/grooves on instrument holder 64 that mates with a corresponding grooves/tabs on the instrument 30) may allow the instrument 30 to be locked at different axial positions in instrument holder 64.

In some embodiments, the bracket 62 and instrument holder 64 may have locks or other mechanisms to lock the endoscope 5 and instrument 30 in a particular position. Further, in some embodiments, the bracket 62 and instrument holder 64 may include stops or other mechanisms to limit the longitudinal displacement of the endoscope 5 and instrument 30. The bracket 62 and instrument holder 64 may be made of any material known in the art and may include any size. In some embodiments, a surface of the bracket 62 and the instrument holder 64 (for instance, a surface that interfaces with the endoscope 5 and the instrument 30) may be coated or covered with a different material to modify the friction between these components. In some embodiments, a separate component (such as, for example, a foam sleeve) may fit around the endoscope 5 and/or the instrument holder 64 to improve holding and protecting the scope.

Figure 5A:
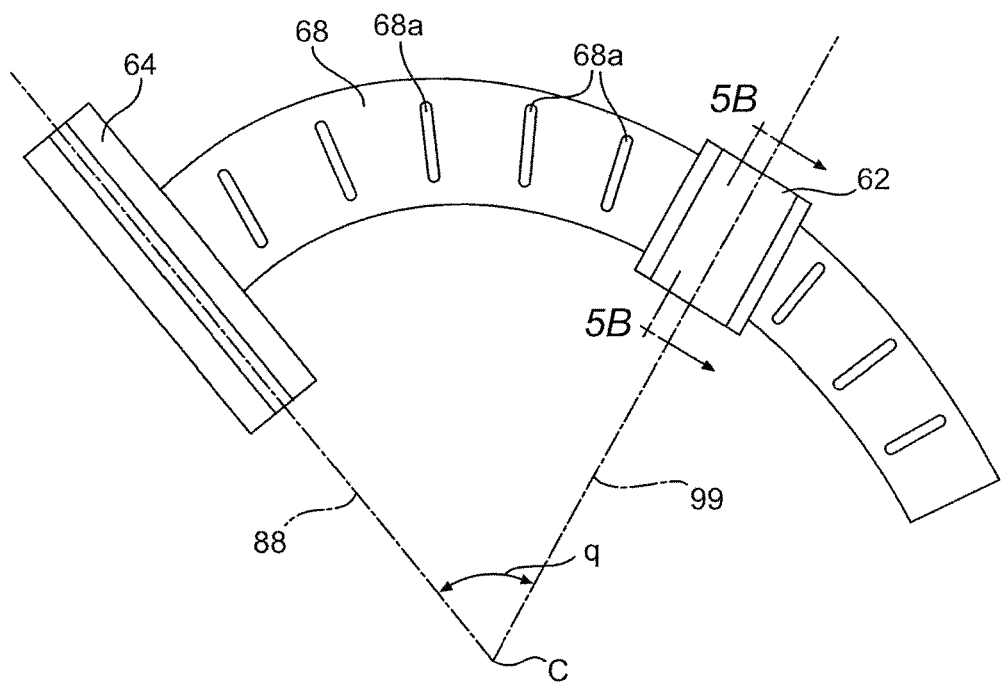
FIG. 5A is an illustration of a top view of apart of the device holder of FIG. 2.
Figure 5B:
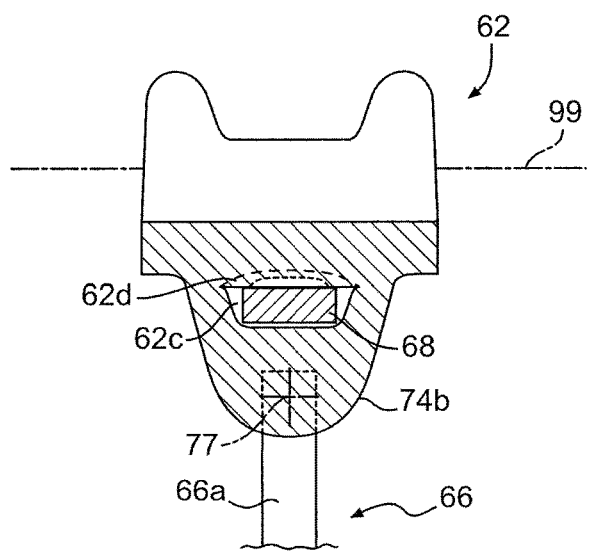
FIG. 5B is a cross-sectional view of a bracket that may be used in the device holder of FIG. 2.

With reference to FIG. 2, the bracket 62 and the holding device 64 may be coupled together by an arm 68. FIG. 5A illustrates a top view of the bracket 62 and the instrument holder 64 coupled together by arm 68. FIG. 5B illustrates a cross-sectional view of the bracket 62 and the arm 68 along a plane identified in FIG. 5A. In the discussion below, reference will be made to FIGS. 2, 5A, and 5B. Arm 68 may orient the instrument holder 64 such that the longitudinal axis 99 (of the elongate member 20) of an endoscope 5 coupled to the bracket 62 intersects the central axis 88 of an instrument 30 coupled to instrument holder 64 at a point C. In some embodiments, as illustrated in FIG. 2, arm 68 may have the shape of an arc of a circle with C as the center and axes 99 and 88 as radii. In some embodiments, the arm 68 may maintain a fixed spacing between the bracket 62 and the instrument holder 64, while in other embodiments, the arm 68 may be configured to change the spacing between the bracket 62 and the instrument holder 64. The spacing between the bracket 62 and the instrument holder 64 may be varied by any means known in the art. In an exemplary embodiment, one or both of instrument holder 64 and bracket 62 may be slidably coupled to arm 68.

In one such embodiment, as illustrated in FIG. 5B, arm 68 may pass through a slot 62c on bracket 62 such that the bracket 62 may move along the arm 68 to vary the spacing between the bracket 62 and the instrument holder 64. Arm 68 may have features, such as, for example, ridges 68a, that mate with corresponding features on the bracket 62 to lock the bracket 62 at desired positions in the arm 68. In some embodiments, these ridges 68a may be small protrusions that fit into corresponding grooves 62d in the bracket 62. A mechanical force may be applied to the bracket 62 to slide the bracket 62 on the arm 68. When the applied force exceeds a threshold value, a ridge 68a may separate from groove 62d, allowing the bracket 62 to slide on the arm 68. The arm 68 may include multiple ridges 68a positioned such that the bracket 62 may be located at multiple locations on the arm 68. In some embodiments, these multiple ridges 68a may be located such that the angle $\theta$ between longitudinal axis 99 and central axis 88 may be changed in fixed increments. In some embodiments, in place of ridges 68a, arm 68a may include slots or holes to position and secure bracket 62 to different locations on arm 68. In some embodiments, in place of ridges 68a, other mechanisms (such as, for example, a set-screw) may be used to position and lock bracket 62 at any location on arm 68. In such embodiments, the angle $\theta$ between longitudinal axis 99 and central axis 88 may be changed to any value. Additionally or alternatively, in some embodiments, instrument holder 64 may include features (such as slot 62c on bracket 62 or other features) that enable the instrument holder 64 to be moved along arm 68 to vary the spacing between the instrument holder 64 and the bracket 62. It is also contemplated that, in some embodiments, bracket 62 may include features or components adapted for improved ergonomics (such as, for example, non-planar components and/or surfaces).

Figure 6:
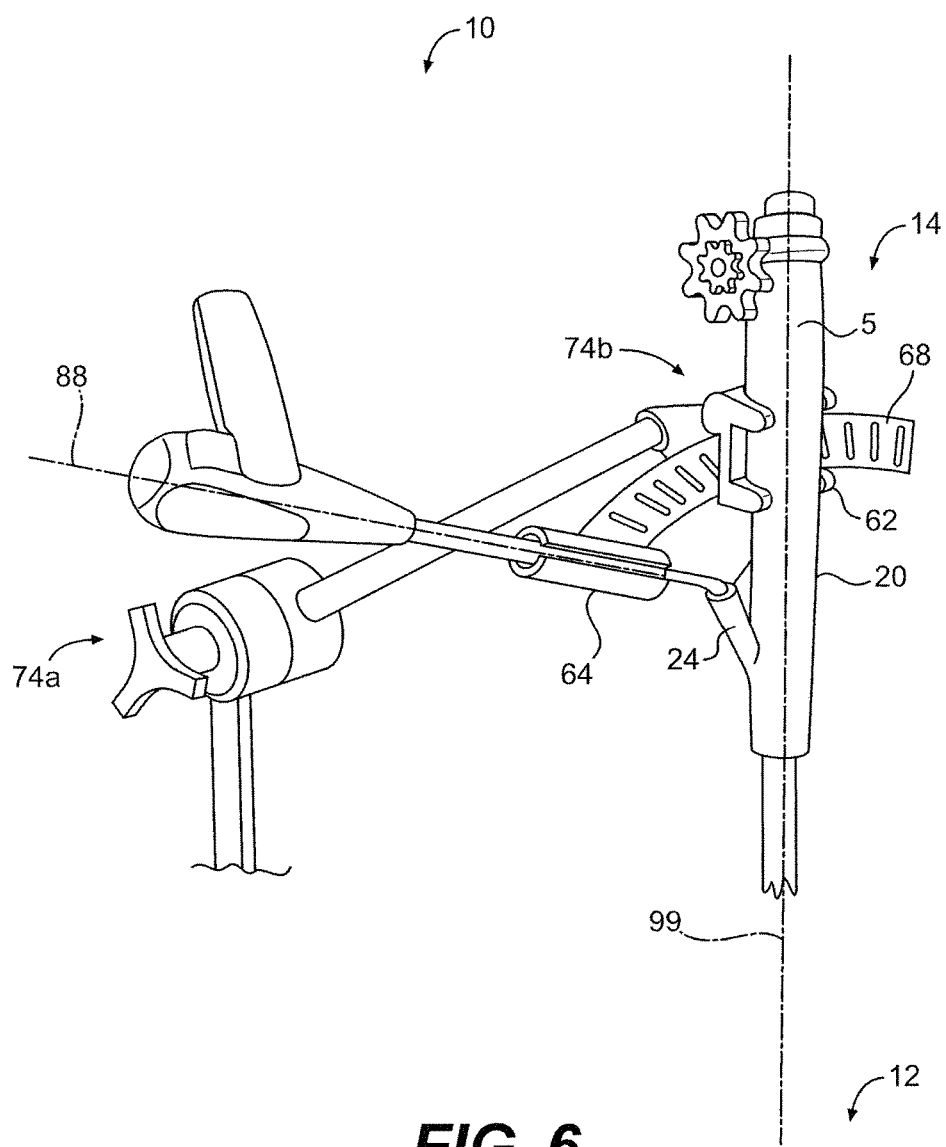
FIG. 6 is a perspective view of the endoscopy system of FIG. 1A in a different orientation.

As best seen in FIG. 5B, in some embodiments, the bracket 62 (or the arm 68) may coupled to the adjustable support 66 (such as, for example, member 66a of adjustable support 66) though a hinge 74b. Hinge 74b may be configured to rotate the bracket 62 (along with arm 68) about an axis 77 that extends into the plane of the paper. In addition to rotating the bracket 62 and the arm 68 using hinge 74a (see FIG. 2), rotating the bracket 62 on hinge 74b may allow the endoscope 5 coupled to bracket 62, and the instrument 30 coupled to instrument holder 64, to be rotated about axis 77. FIG. 6 illustrates the endoscopy system 10 of FIG. 1 in which the spacing between the bracket 62 and the instrument holder 64 is increased and the bracket 62 and the instrument holder 64 have been rotated about hinge 74a and 74b to point the distal end 12 of endoscopy system 10 down.

Although, in the discussion above, an endoscope 5 and an instrument 30 are described as being coupled to the bracket 62 and the instrument holder 64 respectively, in general, any type of tool may be coupled to the bracket 62 and instrument holder 64. The ability to change the spacing and the angle between the bracket 62 and the instrument holder 64 may allow for divergence of the instruments coupled thereto at a proximal end while allowing these instruments to converge along a center line at the distal end. Such an ability may allow the surgeon to position these instruments in the most ergonomic manner for the type of procedure being performed. The ability to rotate the instruments as one and point them in any direction may also increase the efficiency of the procedure.

A method of applying a holding device of the current disclosure may include a surgeon inserting a distal end 12 (of the elongate member 20) of an endoscope 5 into the body of a patient through an opening. The surgeon may push the elongate member 20 into the body to position the distal end 12 at a desired location within the body. An imaging device associated with the endoscope 5 may enable the surgeon to suitably position the endoscope 5 within the body. The surgeon may now configure the holding device 60 to support the endoscope 5. Configuring the holding device 60 may include adjusting the height and the orientation (such as, the angular orientation) of the top section 72 of the holding device 60 using the telescoping section and the hinges (such as hinge 74a, 74b, etc.) of the adjustable support 66. The surgeon may support the endoscope 5 on the holding device 60 by securing a distal portion of the endoscope 5 in bracket 62. The surgeon may then insert the distal end of instrument 30 into a port 24 that extends at an angle from of the endoscope 5, and push the instrument 30 down the port 24. As the instrument 30 is pushed in, the relatively more flexible distal portion 38 of the instrument 30 may bend to allow the instrument 30 to turn and enter a channel 22 that extends longitudinally through elongate member 20. The surgeon may push the instrument 30 down the elongate member 20 until the end effector 32 at the distal end of the instrument 30 is positioned at a desired location in the body.

The surgeon may then support the instrument 30 on the holding device 60 by securing a relatively rigid proximal portion 36 of the instrument 60 on instrument holder 64. To suitably orient instrument 30 with respect to the endoscope 5, the surgeon may increase or decrease a spacing between the bracket 62 and the instrument holder 64. When the spacing is increased (or decreased), as illustrated in FIG. 6, a portion of the flexible distal portion 38 of the instrument 30 that is external to port 24 may bend to allow the proximal end of the instrument 30 to diverge from the proximal end of endoscope 5. Changing the spacing between the bracket 62 and the instrument holder 64 allows the proximal ends of the endoscope 5 and the instrument 30 to diverge from each other while their distal ends extend along a common axis.

Figure 7:
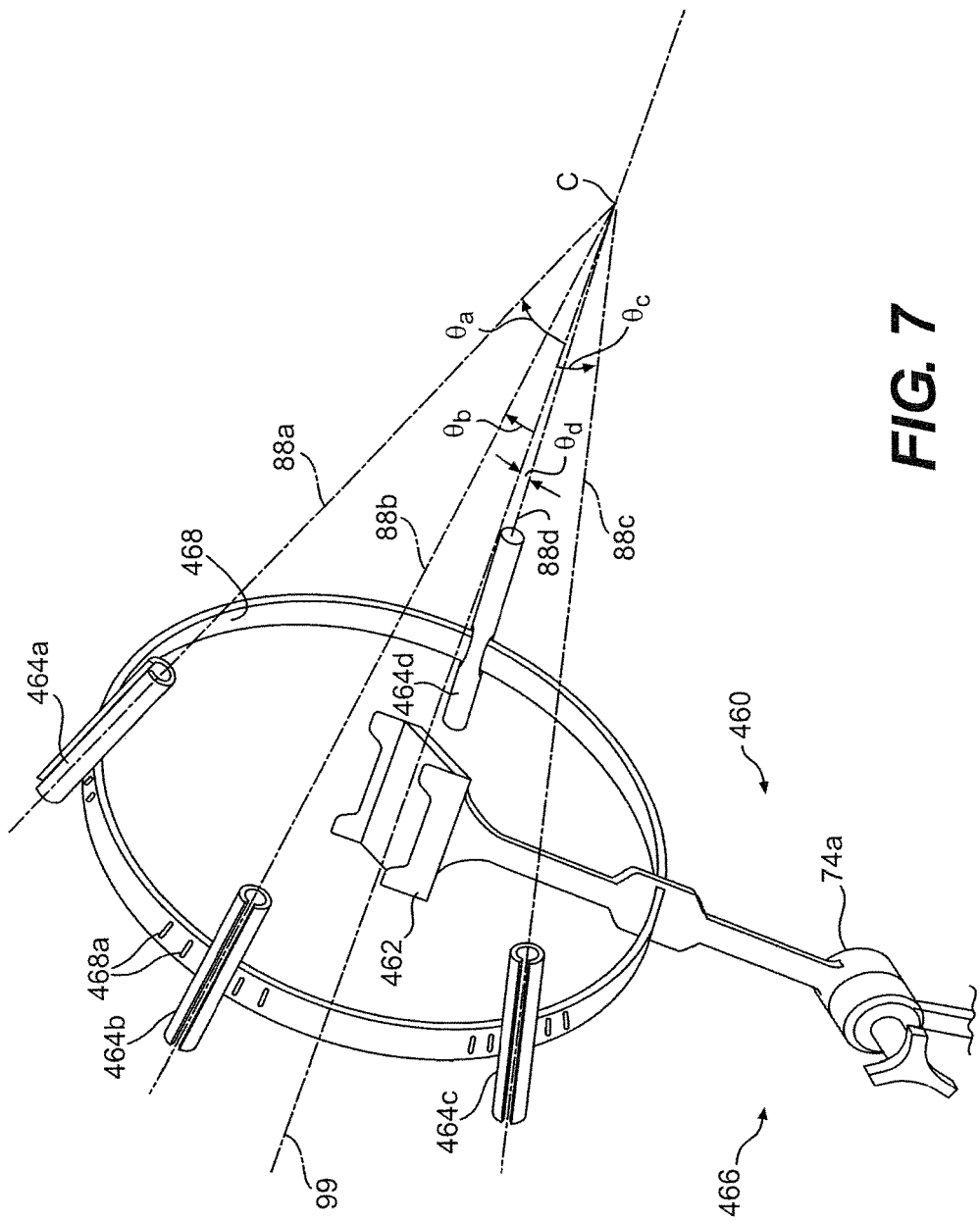
FIG. 7 is a perspective view of another embodiment of a device holder.

As described previously, a holding device of the current disclosure may include any number of brackets and/or holding devices. FIG. 7 illustrates an embodiment of holding device 460 which includes four instrument holders 464a, 464b, 464c, 464d slidably mounted on a ring shaped arm 468 positioned around a bracket 462. During operation, these instrument holders (464a, 464b, 464c. 464d) may support instruments 30 and bracket 462 may support an endoscope (or another device). These instruments and endoscope have been removed from the instrument holders and the bracket of FIG. 7 for clarity. The ring may include ridges 468a that act as locking mechanisms to lock the instrument holders 464a, 464b, 464c, 464d at desired locations. The instrument holders may be oriented such that the central axes 88a, 88b, 88c, 88d of instruments coupled thereto intersects a longitudinal axis 99 (of the elongate member 20 of an endoscope 5 coupled to the bracket 462) at a location C. Although FIG. 7 illustrates the central axes 88a, 88b, 88c, 88d intersecting longitudinal axis 99 at the same location, this is not a requirement. These central axes 88a, 88b, 88c, 88d may make angles $\theta_a$, $\theta_b$, $\theta_c$, and $\theta_d$ respectively with longitudinal axis 99. Angles $\theta_a$, $\theta_b$, $\theta_c$, and $\theta_d$ may be the same or they may be different. During use, different instruments may be coupled to the instrument holders 464a, 464b, 464c, 464d, and an endoscope having multiple channels may be coupled to bracket 462. The elongate member 20 may include multiple ports to direct the distal ends of each instrument to a channel. The angle that a central axis makes with the longitudinal axis may correspond with the angle a port makes with the longitudinal axis. In embodiments where the ports are located at substantially the same location along the longitudinal axis 99 of the elongate member, the instrument holders 464a, 464b, 464c, and 464d may be oriented such that they intersect at substantially the same location along the longitudinal axis 99. Although FIG. 6 illustrates the multiple instrument holders (464a, 464b, 464c, 464d) mounted on a ring shaped arm 468, this is not a requirement, and in other embodiments, each instrument holder may include its own support.

The various components of the endoscopy system 10 described herein may be made of a suitable biocompatible material. Some or all of these components may also be flexible to traverse tortuous anatomy in the body. Any aspect set forth in any embodiment may be used with any other embodiment set forth herein. Every device and apparatus set forth herein may be used in any suitable medical procedure, may be advanced through any suitable body lumen and body cavity, and may be used to visualize, acquire, or remove tissue from any suitable body portion.

It will be apparent to those skilled in the art that various modifications and variations can be made in the disclosed systems and processes without departing from the scope of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims and their equivalents.

What is claimed is:

1. A system comprising:
    a medical device including a channel and a port in communication with the channel;
    an instrument insertable into the port of the medical device to extend within the channel towards a distal end of the medical device;
    a bracket supporting a proximal portion of the medical device, wherein the bracket is proximal to the port of the medical device;
    a holder supporting a proximal portion of the instrument, such that a central axis of the instrument intersects a longitudinal axis of the medical device, wherein the instrument includes a distal end effector, such that advancing the instrument distally through the channel allows the end effector to exit the medical device; and
    an arm coupling the bracket to the holder.

2. The system of claim 1, wherein the medical device is secured between a first extension and a second extension of the bracket.

3. The system of claim 2, wherein the first extension is moveable relative to the second extension along an axis transverse to a longitudinal axis of the medical device.

4. The system of claim 2, wherein at least one of the first extension or the second extension is resilient to secure the medical device between the first and second extensions with frictional force.

5. The system of claim 1, wherein the port is angled relative to the channel, and wherein a position of at least one of the bracket or the holder is adjustable relative to the arm to adjust an angle between the proximal portion of the medical device and the proximal portion of the instrument.

6. The system of claim 1, wherein the bracket includes a first mating element and the arm includes a plurality of second mating elements complementary to the first mating element, such that a position of the bracket is adjustable by sliding the bracket along a length of the arm to engage the first mating element with one of the second mating elements.

7. The system of claim 1, wherein the holder includes a first extension and a second extension configured to flex away from, and towards, each other for receiving the instrument therebetween, and wherein the instrument is flexible.

8. The system of claim 1, further comprising an adjustable support coupled to the arm, wherein the bracket is rotatable relative to the support.

9. A system comprising:
    a medical device including a channel and a port in communication with the channel, the port being angled relative to the channel;
    an instrument insertable into the port of the medical device, such that the instrument extends within the channel of the medical device towards a distal end of the medical device to allow a distal end of the instrument to exit the channel;
    a bracket supporting a proximal portion of the medical device, wherein the bracket is proximal to the port of the medical device, and wherein the medical device is secured between a first extension and a second extension of the bracket, the second extension being movable relative to the first extension;

a holder supporting a proximal portion of the instrument, such that a central axis of the instrument intersects a longitudinal axis of the medical device; and an arm coupling the bracket to the holder.

10. The system of claim 9, wherein the instrument is flexible, and wherein the distal end of the instrument includes an end effector, such that advancing the instrument distally through the channel allows the end effector to exit the medical device.

11. The system of claim 9, wherein a position of at least one of the bracket or the holder is adjustable relative to the arm to adjust an angle between the proximal portion of the medical device and the proximal portion of the instrument.

12. The system of claim 11, wherein the arm includes a plurality of slots for receiving each of the bracket and the holder, the arm being curved to adjust an angle between the bracket and the holder.

13. A system comprising:

a medical device including a channel and a port in communication with the channel, wherein a proximal portion of the medical device includes controls for steering a distal end of the medical device;

an instrument insertable into the port of the medical device to extend within the channel towards the distal end of the medical device;

a bracket supporting the proximal portion of the medical device, wherein the bracket is proximal to the port of the medial device;

a holder supporting a proximal portion of the instrument, such that a central axis of the instrument intersects a longitudinal axis of the medical device; and an arm coupling the bracket to the holder.

14. The system of claim 13, wherein the medical device is secured between a first extension and a second extension of the bracket, the first extension being moveable relative to the second extension along an axis transverse to a longitudinal axis of the medical device.

15. The system of claim 14, wherein the medical device is secured between the first and second extensions with frictional force.

16. The system of claim 13, wherein a position of at least one of the bracket or the holder is adjustable relative to the arm to adjust an angle between the proximal portion of the medical device and the proximal portion of the instrument.

17. The system of claim 13, wherein the arm is curved and includes a plurality of slots for receiving each of the bracket and the holder to adjust an angle between the proximal portion of the medical device and the proximal portion of the instrument.

* * * * *